United States Patent [19]

Redman et al.

[11] Patent Number: 5,200,418
[45] Date of Patent: Apr. 6, 1993

[54] CRYPTOSPORIDIOSIS AMELIORATION

[75] Inventors: Donald R. Redman, Wooster, Ohio; James E. Fox, Norcross, Ga.

[73] Assignees: The Ohio State University, Columbus, Ohio; Rhone-Poulenc Inc., Monmouth Junction, N.J.

[21] Appl. No.: 728,875

[22] Filed: Jul. 12, 1991

[51] Int. Cl.$^5$ .............................................. A61K 31/47
[52] U.S. Cl. ................................................. 514/311
[58] Field of Search ....................................... 514/311

[56] References Cited

U.S. PATENT DOCUMENTS 3,485,845  12/1969  Davis et al. .................. 260/287

OTHER PUBLICATIONS

*Bovine Veterinary Forum*, Focus: Cryptosporidiosis, Apr. 1990, vol. 5, No. 1, pp. 1-16.
Deccox® Product Summary, trade literature of Rhone-Poulenc, technical Manual pp. 1-8.
Kirkpatrick et al., "Cryptosporidiosis" Continuing Education Article #9, *The Compendum on Continuing Education*, vol. 6, No. 3, Mar. 1984, pp. S154-S164.
J. A. Moore et al., "Cryptosporidiosis in Animals Including Humans", Continuing Education Article #1, *Compendum Small Animal*, vol. 10, No. 3, Mar. 1988, pp. 275-283.
K. W. Angus et al., "Prophylatic effects of anticoccidial drugs in experimental murine cryptosporidiosis", *The Veterinary Record*, Feb. 18, 1984, pp. 166-168.
"Management of Cryptosporidiosis", J. Antimicrobial Chemotherapy, V. 15, 1985, pp. 3-4.

*Primary Examiner*—Leonard Schenkman
*Attorney, Agent, or Firm*—Frank H. Foster

[57] ABSTRACT

This invention relates to the amelioration of cryptosporidiosis symptoms, such as diarrhea, caused by the parasite crypotosporidium in susceptible host animals using effective amounts of decoquinate.

5 Claims, No Drawings

CRYPTOSPORIDIOSIS AMELIORATION

TECHNICAL FIELD

This invention relates to Crypotosporidium, a genus of protozoan parasites, and to crytosporidiosis, an infection caused by this parasite in various hosts, and to a method of treatment for alleviation or amelioration of clinical symptoms accompanying an infected host. More particularly, the invention concerns hosts, such as various animals including human, susceptible to infection by *Cryptospordia oocysts* and treating such hosts with decoquinate in a dosage effective to ameliorate clinical signs, such as diarrhea, accompanying the cryptosporidiosis infected host, and generally administering such dosage with an initial administration, at least for neonatal ruminants, within three-days of birth and daily thereafter until approximating about when a normal neonatal calf may be weaned, or administering for up to 3 to 6 weeks generally.

BACKGROUND ART

Cryptosporidiosis is caused by a protozoa coccidia of the suborder Eimeriorina, family Crypotospordidae, genus cryptosporidium. Cryptosporidial species differ from conventionally recognized coccidia (such as Eimeria and isosporia spp.) in at least four ways: (1) Crypotosporidium spp. are much smaller (4 to 6 μm in diameter); (2) although they are thought to invade the epithelia cells of the microvillous border of the intestinal and respiratory tract, they do not invade deep into the tissues like coccidia; (3) in contrast to coccidiosis, there currently are no drugs available for treating cryptosporidiosis; and (4) coccidia are considered host specific, whereas Cryptosporidium spp. are not considered to be host specific.

Although Cryptosporidium has been reported sporadically in the literature for about the past eighty years, only within about the past several decades has it become recognized as a cause of entercolitus in various animals and humans. The cryptosporidia that commonly parasitize the intestinal tracts of calves and humans have been shown to readily infect calves, humans, lambs, piglets and newborn mice. The host range probably includes most newborn mammals. The potential for spread between species, particularly among newborn animals and to humans is well documented.

Intestinal cryptosporidiosis is transmitted directly by the fecal-oral route. Infected individuals shed oocysts in their feces. In contrast to other coccidia, cryptosporidia do not require either an intermediate host or an incubation period outside the host, to sporulate and become infectious. Cryptosporidia are infectious at the time they are shed in feces. One milliliter of diarrheal feces from an infected calf may contain more than 10,000 *cryptosporidia oocysts*. Thus, the infection can be transmitted readily from calf to calf and even to a human worker via the contaminated feces. In food source animals, such as calves and lambs, diarrhea in the second week of life is the main clinical sign of cryptosporidiosis. In the absence of complicating factors, dehydration remains minimal although emaciation may be evident, appetite may or may not be affected, and the diarrhea subsequently abates within about 8–10 days. In addition to the loose stool from the diarrhea, a characteristic is an offensive rancid-like odor of the stool. Stools are frequently of a wet putty-like consistency, creamy yellow to white in color, and occasionally have small flecks of blood. These stools may vary depending on diet and/or the presence of other infectious agents, which typically result in a very watery yellow liquid stool which readily separates into solid and liquid portions. Uncomplicated cryptosporidial infections of calves do not usually result in mortality. Severe diarrhea with profound dehydration and death in lambs in Great Britain has been reported, which suggests a more virulent isolate in Great Britain in comparison to in the United States in which lambs suffer milder cryptosporidiosis. In any event, there generally are complicating factors in the (animal) host infected with cryptosporidiosis, which factors must be overcome. Supportive care may be necessary, warming in winter, extra fluids above the normal (milk) ration, etc. may be needed.

Currently there are no known efficacious drugs available for treating or preventing cryptosporidiosis in man or animals. In animals, the infection usually occurs in the neonate causing an enteropathy resulting in diarrhea, weight loss, emaciation and sometimes death. Frequently animal-meat producers use various products for treating diarrhea caused by Cryptosporida spp. without beneficial effect, sometimes causing more harm than good.

Attempts to find an efficacious product for cryptosporidiosis frequently looked at treating the animal after the infection had occurred or to determine if compounds would prevent infection. Many compounds have been tried and found not to be effective in eliminating Cryptospodidia infection.

SUMMARY OF THE INVENTION

The present invention provides a method of treatment for amelioration of infective symptoms arising in host animals, including humans, from this infection by the Cryptospodidium parasite. The infections generally occur in the host animal from oral take-up of *Cryptosporidia oocysts* and typically are evidenced by clinical signs, such as diarrhea, with amelioration of the duration that infection-imposed diarrhea of importance to the invention's method. The invention's method of treatment generally is administering by the oral route into the host animal of a dosage of decoquinate effective to ameliorate the duration of the diarrhea. The administered dosage amount on a daily basis of the decoquinate is significantly greater, in the order of severalfold (i.e. 5× to 7× greater) than known for decoquinate in normal usage as a coccidiostat for animals. Additionally in contrast to decoquinate being used as a coccidiostat, where as far as known the recommended usages are of manyfold lower dosage levels, when used as a coccidiostat the decoquinate also is administered to significantly older animals, i.e. animals of age well beyond the first several days after birth, then the invention's method. Generally and preferably the invention's method treats the newborn, preferably within one day and within 3 days of birth and daily thereafter for 3 to 6 weeks and with oral dosages of decoquinate significantly larger than advocated for older animals as a coccidiostat.

DETAILED DESCRIPTION

In the invention's method of treatment there is employed a substance whose common name is "Decoquinate" and whose chemical name is "Ethyl 6-(decyloxy)-7 ethoxy-4-hydroxy-3quinolinecarboxylate". The preparation of this compound is described in U.S. Pat. No. 3,485,845, M. Davis et al, wherein a utility of this compound is stated to be "... potent coccidiostat(s) useful in the prevention of coccidiosis in chickens caused by parasites of the genus Eimeria." In so far as any portion to its entirety of the contents and teachings of this U.S. Pat. No. 3,485,845 be necessary to adequately teach the present application's invention, by this reference here thereto, those contents in part to entirety are hereby incorporated in the present invention's disclosure.

The decoquinate is administered to an animal host generally by the same route by which the animal host in its natural lifestyle environment would be challenged and subsequently infected by the Cryptosporidium parasite in the form of its oocysts. This route is the oral route in the animal host and is the most desirable and preferred route for decoquinate administration. Administration by other routes may be useful, but presently would not appear to as economical or easily practiced as proceeding by the oral route.

The active decoquinate rarely would be administered alone to the host, but generally and preferably would be a component (e.g. blended therein) in a composition containing other components, such as food, liquids and innocuous substances, acceptable to the animal host, and preferably would in this manner be administered orally. While in the invention's illustrative specific examples, which follow later, the illustrated administering is of the decoquinate in blended composition contained within a gelatin capsule and by a forceful means of a capsule gun, and while that administering is useful, other administerings are contemplated as useful and preferred. For example, for administering to a neonatal animal host, the inclusion of the decoquinate in the food and/or drink to which the host is accustomed is preferred and believed to be more desirable, as no forceful administration would be needed. In the instance of neonatal animal hosts receiving in whole or part a liquid milk replacement as food, the decoquinate could as minute particles be suspended in the liquid milk replacement. Such suspensions would appear to be preparable by passage of decoquinate along with the liquid milk replacement through a colloidal mill apparatus, useful for preparing colloidal dispersion, and/or by using conventional food additive approved dispersants to disperse the decoquinate in the milk replacement or other liquid for subsequent oral take-up by the host animal.

The amount of decoquinate administered to the animal host is a dosage effective to shorten duration of diarrhea arising in the host from the host becoming infected by cryptosporidium oocysts. The shortening of the duration of diarrhea is evaluated by comparison of an similarly infected untreated like host. Desirably the administered dosage amount is not only effective to shorten the duration of the diarrhea but also effective to shorten the duration of oocysts of Christosporidium found in the host's feces in comparison to the duration of oocysts found in the feces of an untreated similarly infected like host. For expression as a more quantitative dosage amounts, at least as to bovine neonatal calves, a useful active decoquinate dosage for a bovine neonatal (newly born) calf desirably should be 3.7 to 7.7 mg per day per each kg body weight of the calf and more desirably should be 4 to 6 mg daily per each kg body weight of the calf. For other host animals the above numerically expressed daily dosages are expected to be useful, but may not necessarily be the optimum dosages for preferred and/or optimum amelioration results.

The decoquinate most desirably is administered to the animal host when the animal host is at a relatively great risk for infection, i.e. when the immunity resistance of the animal is low and the host is of great susceptibility to infection by Cryptosporidium oocysts. For bovine calves, generally this is at birth and shortly thereafter and runs for some uncertain time period thereafter until approximating when a normal neonatal calf would be weaned. The initial administering of a requisite dosage of decoquinate should be most desirably within one day of birth, preferably within 3 days of birth, and continued on a daily basis up to 3 to 6 weeks. For other susceptible neonatal animals it is believed useful results will be also obtained when the initial administering is within one day of birth and preferably before the animal is 3 days old. Where a low or lowered immunity exists and risk of infection is greater than normal for a particular animal species, such as when the animal host is anemic, with diagnosis of the anemia some significant time after birth, or such that the host has undergone immunosuppression because of reception of particular medical therapy and/or transplant treatment, or such that the animal has an acquired immunodeficiency syndrome, the initial administering contemplated should preferably be made before onset of visually observable clinical symptoms of infection with Cryptosporidiosis, for example persistent diarrhea. For such animals it presently is unknown and uncertainty exists for how long a duration the daily decoquinate administrations should be continued following the initial administering.

In the illustrative EXAMPLES which follow, unless explicitly stated otherwise, the following procedures were used:

Daily from each calf there was collected a stool in a fecal container. The stool in each container then was visually examined and given a code rating as follows:

| ABNORMAL STOOL CODE | STOOL DESCRIPTION |
|---|---|
| 0 | Normal stool, has form or shape with consistency relatively firm. |
| 1 | More fluid and more plastic-like and not as firm as normal stool; circa-putty or caulking material consistency. |
| 2 | Somewhat more fluid (semi-liquid) but not segregated into fluid and solids; circa-pancake batter consistency |
| 3 | Quite watery, possibly contains some blood and may segregate into fluid solid phases upon standing |

Then within each group, the five stool-code ratings were averaged to provide a mean average. Where the means abnormal stool-code was 1 or higher the stool was deemed diarrheic.

The daily stool samples also were examined for the presence of *Cryptosporidia oocysts* and a Crypto Shedding score was determined. This was done by the following: a smear of the daily stool sample was made on a glass slide with an applicator stick-heat fixed and stained with an acid fast stain. This stained smear then was examined visually microscopically at a magnification of at least 100 times. If no oocysts were observed, the sample was rated 0. If oocysts were noted a count was made of the number of oocysts within the field of the microscopic lens and another count made of the number of oocysts in another microscopic field of the smear with this procedure repeated until at least a total of 5 or more dry smear fields had been counted, whereupon the total of counts and fields counted were used to calculate a mean average of oocysts for that particular stool sample. The mean average counts then were given CRYPTO SCORE ratings according to the following code:

| OOCYSTS COUNT | CRYPTO SCORE |
| --- | --- |
| 0-1 | 1 |
| 0-2 | 2 |
| 0-3 | 2 |
| 0-4 | 2 |
| 0-5 | 2 |
| 1-4 | 3 |
| 1-6 | 3 |
| 2-7 | 4 |
| 2-10 | 5 |
| 3-12 | 5 |
| >12 | 5 |

The CRYPTO SCORE reported in the EXAMPLES is the sample's mean average of each day that oocysts were detected.

For administration of the decoquinate, gelatin capsules were filled with the requisite amount decoquinate blended in an amount, 6% by weight decoquinate in a premix of degermitated corn meal containing minor amounts of added soybean oil and lecithin. The administrations were oral with a force feed by capsule gun to the calves. An useful premix containing decoquinate is commercially available, and marketed as DECCOX® Premix by Phone-Poulenc, Atlanta, Ga.

For challenge, viable Cryptosporidia oocysts were obtained from a stool of an experimentally challenged calf. They were stored in 2% potassium dichromate until use. Within four weeks of obtaining the oocysts they were washed in water, concentrated by centrifugation procedures, counted and treated with 25.% peracetic acid and washed again. The delivery dose was drawn into a sterile 1000 syringe. The dose was administered orally using a 8" length of plastic tube attached to the syringe with the tube extending into the throat of the calf.

In the Examples, calves were fed twice daily with a water-reconstituted commercially available nonmedicated powdered milk for calves. The supplied feed amount per calf was that which was recommenced by the powdered-milk manufacturer with the same amount supplied for each calf.

EXAMPLE A

Ten neonatal Holstein bull calves, typically each weighing 85±15 lbs, were used to evaluate the anticryptosporidial effect of decoquinate. Five calves served as controls and 5 were treated with 225 mg decoquinates in gelatin capsule per feeding until completion of trial (8 wks). Calves were orally exposed with $8.5 \times 10^5$ Cryptosporidian oocysts at 4 days of age. The average number of days from exposure to onset of shedding was 4.4 for controls and 5.8 for treated calves. Number of days with abnormal stool was 18.6 for controls and 3.6 for treated calves. Average daily gain was 1.496 lbs/day for controls and 1.116 lbs/day for treated calves for the 8 wks. Average daily gain first 3 wks. (period at highest risk) was 0.6760 for controls and 0.8122 for treated calves. Treatment with decoquinate did not prevent shedding of Cryptosporidia oocysts. It was shown that treatment may delay the time from exposure to shedding, reduce the number of days shedding, and improve the stool consistency score. The lack of a more beneficial response in weight gains could not be explained, although it may be related to the dose level of decoquinate used (circa-10× recommended levels for treatment of coccidiosis in cattle).

Summarizing in this EXAMPLE A, 5 calves were treated from birth with 112.5 mg decoquinate per feeding (2 feedings daily=225 mg daily decoquinate) for 8 weeks and five calves as controls. At four days of age, all calves were challenged with $8.5 \times 10^5$ Cryptosporidia oocysts. Decoquinate did not prevent shedding of Cryptosporidia oocysts. It was shown that treatment may have delayed the time from exposure to onset of shedding, did reduce the number of days shedding and did improve the stool consistency score.

EXAMPLE B

A second evaluation was conducted to determined the effect of varying levels of decoquinate on experimental Cryptosporidia infection in neonatal Holstein bull calves. This example employed four groups off five bull calves per group, the four groups being controls, 52.5, 105, and 210 mg decoquinate in gelatin capsules per feeding (2 feedings per day) for four weeks. Three days after starting the trial, calves were orally challenged with $8.5 \times 10^5$ viable Cryptosporidia oocysts. Calves were penned individually, fed a commercially available nonmedicated milk replacer, observed twice daily and daily stool samples were collected, scored and examined for oocyst shedding. weight gain was also measured. When indicated, samples were checked for other enteropathogens, i.e., Coccidia, rotavirus, enterotoxigenic E. coli.

Because of space and availability of calves, the evaluation was conducted in two phases with calves being assigned to the experimental groups on a randomized basis. The calves were obtained through a local supplier to veal calf facilities, with a request that they originate from the least number of farms as possible and must be assembled and available with an 8 hour period. All obtained calves were less than 4 days old with individual calves weighing as low as 70 lbs (31.8 kg) to 100 lbs (45.5 kg) and for all obtained calves a mean average weight of ~90 lbs (~40.9 kg).

The results of the evaluation by groups, i.e. controls, 52.5, 105 and 210mg decoquinate dosage, respectively, each feeding, are shown in TABLES 1-4. TABLES 5-9 show the results for: TABLE 5—days to first shedding, TABLE 6—Number of days shed, TABLE 7—Cryptosporidia shedding score, TABLE 8—number of days with abnormal stool score, and TABLE 9—Average daily weight gain.

In general, there was found a beneficial response to the treatment up to the 105 mg dosage (~10×) level, except the number of days to first shedding was not improved at the 52.5 mg level (~5×). In contrast, the responses at the 210 mg (·20×) level were all very similar to the controls. The reason for the lack of a beneficial response at the 20× level could not be explained.

The result of the trials, support that a beneficial clinical response is obtained using decoquinate with experimental cryptosporidial infections.

In the tables, which follow, DA=day or days, as most appropriate.

TABLE 1

RESPONSE OF CONTROL CALVES TO CHALLENGE WITH $8.5 \times 10^5$ CRYPTOSPORIDIA OOCYSTS.

| CALF # | DA TO 1ST SHEDDING | # DA SHED | CRYPTO SCORE | DA ABNORMAL STOOL CODE | TOTAL WT GAIN | AVG DAILY GAIN |
|---|---|---|---|---|---|---|
| 4 | 5 | 7 | 1.33 | 5 | 9 | .31 |
| 10 | 4 | 6 | 2.00 | 3 | 6 | .21 |
| 12 | 4 | 10 | 2.80 | 3 | 11 | .38 |
| 22 | 4 | 5 | 3.00 | 3 | 17 | .59 |
| Mean | 4.25 | 7 | 2.2825 | 3.5 | 10.75 | .37 |

TABLE 2

RESPONSE OF CALVES TREATED WITH 52.5 MG DECOQUINATE PER FEEDING AND CHALLENGED WITH $8.5 \times 10$ CRYPTOSPORIDIA OOCYSTS.

| CALF # | DA TO 1ST SHEDDING | # DA SHED | CRYPTO SCORE | DA ABNORMAL STOOL CODE | TOTAL WT GAIN | AVG DAILY GAIN |
|---|---|---|---|---|---|---|
| 1 | 3 | 6 | 2.00 | 0 | 16 | .55 |
| 5 | 3 | 9 | 3.22 | 2 | 11 | .38 |
| 11 | 3 | 1 | 1.00 | 1 | 14 | .48 |
| 13 | 5 | 9 | 2.11 | 3 | 13 | .45 |
| 19 | 4 | 4 | 1.00 | 0 | 16 | .55 |
| Mean | 3.6 | 5.8 | 1.866 | 1.22 | 14 | .48 |

TABLE 3

RESPONSE OF CALVES TREATED WITH 105 MG DECOQUINATE PER FEEDING AND CHALLENGED WITH $8.5 \times 10^5$ CRYPTOSPORIDIA OOCYSTS.

| CALF # | DA TO 1ST SHEDDING | # DA SHED | CRYPTO SCORE | DA ABNORMAL STOOL CODE | TOTAL WT GAIN | AVG DAILY GAIN |
|---|---|---|---|---|---|---|
| 2 | 10 | 1 | 1.00 | 0 | 16 | .55 |
| 6 | 3 | 3 | 3.00 | 0 | 19 | .66 |
| 8 | 5 | 1 | 1.00 | 1 | 11 | .38 |
| 14 | 3 | 7 | 1.85 | 3 | 24 | .83 |
| 17 | 4 | 5 | 1.60 | 0 | 12 | .41 |
| 20 | 5 | 2 | 1.50 | 0 | 24 | .83 |
| Mean | 5 | 3.16 | 1.658 | .67 | 17.6 | .61 |

TABLE 4

RESPONSE OF CALVES TREATED WITH 210 MG DECOQUINATE PER FEEDING AND CHALLENGED WITH $8.5 \times 10^5$ CRYPTOSPORIDIA OOCYSTS.

| CALF # | DA TO 1ST SHEDDING | # DAY SHED | CRYPTO SCORE | DA ABNORMAL STOOL CODE | TOTAL WT GAIN | AVG DAILY GAIN |
|---|---|---|---|---|---|---|
| 3 | 3 | 4 | 1.25 | 2 | −7 | −.24 |
| 9 | 3 | 9 | 2.71 | 2 | 18 | .62 |
| 7 | 3 | 9 | 3.33 | 4 | 18 | .62 |
| 18 | 4 | 7 | 3.43 | 7 | 2 | .07 |
| 21 | 4 | 1 | 4.00 | 0 | 17 | .59 |
| Mean | 3.4 | 6 | 2.944 | 3 | 9.6 | .33 |

TABLE 5

NUMBER OF DAYS TO OOCYST SHEDDING BETWEEN DECOQUINATE TREATED AND CONTROL CALVES CHALLENGED WITH CRYPTOSPORIDIUM OOCYSTS.

| | CONTROLS | 52.5 mg | 105 mg | 210 mg |
|---|---|---|---|---|
| | 5 | 3 | 10 | 3 |
| | 4 | 3 | 3 | 3 |
| | 4 | 3 | 5 | 3 |
| | 4 | 5 | 3 | 4 |
| | | 4 | 4 | 4 |
| | | | 5 | |
| Mean | 4.25 | 3.6 | 5 | 3.4 |

TABLE 6

TOTAL NUMBER OF DAYS OF OOCYST SHEDDING BETWEEN DECOQUINATE TREATED AND CONTROL CALVES CHALLENGED WITH CRYPTOSPORIDIUM OOCYSTS.

| | CONTROLS | 52.5 mg | 105 mg | 210 mg |
|---|---|---|---|---|
| | 7 | 6 | 1 | 4 |
| | 6 | 9 | 3 | 9 |
| | 10 | 1 | 1 | 9 |
| | 5 | 9 | 7 | 7 |
| | | 4 | 5 | 1 |
| | | | 2 | |
| Mean | 7 | 5.8 | 3.16 | 6 |

TABLE 7

CRYPTOSPORIDIUM SHEDDING SCORES OF DECOQUINATE TREATED AND CONTROL CALVES CHALLENGED WITH *CRYPTOSPORIDIUM OOCYSTS*.

|  | CONTROLS | 52.5 mg | 105 mg | 210 mg |
|---|---|---|---|---|
|  | 1.33 | 2 | 1 | 1.25 |
|  | 2 | 3.22 | 3 | 2.71 |
|  | 2.8 | 1 | 1 | 3.33 |
|  | 3 | 2.11 | 1.85 | 3.43 |
|  |  | 1 | 1.6 | 4 |
|  |  |  | 1.5 |  |
| Mean | 2.28 | 1.866 | 1.658 | 2.944 |

TABLE 8

NUMBER OF DAYS OF ABNORMAL STOOL SCORES DURING OOCYST SHEDDING IN DECOQUINATE TREATED AND CONTROL CALVES.

|  | CONTROLS | 52.5 mg | 105 mg | 210 mg |
|---|---|---|---|---|
|  | 5/7 | 0/6 | 0/1 | 2/4 |
|  | 3/6 | 2/9 | 0/3 | 2/9 |
|  | 3/10 | 1/1 | 1/1 | 4/9 |
|  | 3/5 | 3/9 | 3/7 | 7/7 |
|  |  | 0/4 | 0/5 | 0/1 |
|  |  |  | 0/2 |  |
| Mean | 3.5 | 1.2 | .67 | 3 |

TABLE 9

AVERAGE DAILY GAIN BETWEEN DECOQUINATE TREATED AND CONTROL CALVES CHALLENGED WITH *CRYPTOSPORIDIUM OOCYSTS*.

|  | CONTROLS | 52.5 mg | 105 mg | 210 mg |
|---|---|---|---|---|
|  | .31 | .55 | .55 | −.24 |
|  | .21 | .38 | .66 | .62 |
|  | .38 | .48 | .38 | .62 |
|  | .59 | .45 | .83 | .07 |
|  |  | .55 | .41 | .59 |
|  |  |  | .83 |  |
| Mean | .3725 | .482 | .61 | .33 |

Although the invention in the preceding disclosure has been taught and illustrated by example by employment in the invention's method of the active agent of decoquinate, i.e. Ethyl6-n-decyloxy-7-ethoxy-4-hydroxyquinoline-3-carboxylate, a number of other substituted hydroxyquinolinecarboxylates are contemplated as useful in the inventions method. More particularly, such several compounds are taught and claimed in the aforementioned U.S. Pat. No. 3,485,845, M. Davis et al, and are defined by the formula

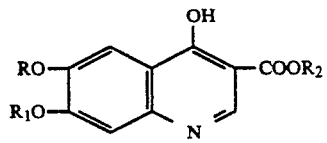

in which R is n-alkyl of 8 to 10 carbon atoms, $R_1$ is methyl, ethyl, n-propyl, isopropyl, or sec-butyl, and $R_2$ is methyl or ethyl, and their non-toxic salts. Each of these several compounds as just defined, are contemplated as having at least some utility in the method of the invention, when employed in whole or part for, or in admixture, with the illustrated herein employed decoquinate, although the extent of amelioration of Cryptosphoridiosis that is realized may be greater or less than that provided by employing decoquinate in the invention's method.

While certain preferred embodiments of the present invention have been disclosed in detail, it is to be understood that various modifications may be adopted without departing from the spirit of the invention or scope of the following claims.

We claim:

1. A method of amelioration of cryptosporidiosis symptoms in a neonatal bovine host exposed to and susceptible to infection by *cryptosporidium oocysts*, which method comprises:
   administering daily and orally decoquinate to said host with an initial daily administration of the decoquinate within 3 days of birth and followed by subsequent daily administrations of the decoquinate for 3 to 6 weeks and in a daily total dosage of an amount which is nontoxic and effective to shorten duration of diarrhea of said host arising from said infection in comparison to a like infected but untreated host.

2. The method of claim 2 in which said daily total dosage is an amount effective also to shorten the duration of said oocysts being found in feces vacated by the host in comparison to a like but untreated host.

3. The method of claim 2 i which the daily administrations are of 3.7 to 7.7 mg of decoquinate per kilogram of body weight of the host.

4. The method of claim 2 in which said dosage daily administered is 4 to 6 mg per kilogram of body weight of said bovine calf.

5. The method of claim 3 in which said administering daily and orally of decoquinate includes several daily administrations, each daily administration separately of a fraction of the amount of the daily total dosage and together totalling the amount of the daily total dosage.

* * * * *

UNITED STATES PATENT AND TRADEMARK OFFICE
CERTIFICATE OF CORRECTION

PATENT NO. : 5,200,418

DATED : April 6, 1993

INVENTOR(S) : Donald R. Redman and James E. Fox

It is certified that error appears in the above-identified patent and that said Letters Patent is hereby corrected as shown below:

Column 1, line 5, for "Crypotosporidium" read --*Cryptosporidium*--; line 6, for "crytosporidiosis" read --cryptosporidiosis--; line 12, for "*Cryptospordia oocysts*" read --cryptosporidia oocysts--; line 24, for "Crypotospordidae" read --cryptosporididae--; line 28, for "Crypotosporidium" read --*Cryptosporidium*--. Column 2, line 22, for "Cryptosporida" read --cryptosporidia--; line 30, for "Cryptospodidia" read --cryptosporidial--; line 37, for "Cryptospodidium" read --*Cryptosporidium*--; line 55, for "then" read --than--. Column 3, line 17, between "to" and "as" insert --be--; line 54, for "Christosporidium" read --*Cryptosporidium*--. Column 5, line 36, for "Phone-Poulenc" read --Rhone-Poulenc--; line 51, for "recommenced" read --recommended--; line 62, for "*Cryptosporidian oocysts*" read --cryptosporidia oocysts-- Column 6, line 14, between "calves" and "as" insert --served--; line 23, for "determined" read --determine--; line 25, for "Cryptosporidia" read --cryptosporidial--; line 26, for "off" read --of--; line 35, for "weight" read --Weight--; line 45, for "with" read --within--.

UNITED STATES PATENT AND TRADEMARK OFFICE
CERTIFICATE OF CORRECTION

PATENT NO. : 5,200,418

DATED : April 6, 1993

INVENTOR(S) : Donald R. Redman and James E. Fox

It is certified that error appears in the above-identified patent and that said Letters Patent is hereby corrected as shown below:

Column 9, line 47, insert a space between "Ethyl" and "6-n-decyloxy-7-ethoxy-4-hydroxyquinoline-3-carboxylate". Column 10, line 17, for "Cryptosphoridiosis" read --cryptosporidiosis--; Claim 2, line 39, for "2" read --1--.  Claim 3, line 43, for "i" read --in--.

Signed and Sealed this

Eighteenth Day of January, 1994

*Attest:*

BRUCE LEHMAN

*Attesting Officer*   *Commissioner of Patents and Trademarks*